United States Patent
Sethuraman et al.

(10) Patent No.: US 11,666,305 B2
(45) Date of Patent: Jun. 6, 2023

(54) WORKFLOW ASSISTANCE FOR MEDICAL DOPPLER ULTRASOUND EVALUATION

(71) Applicant: KONINKLIJKE PHILIPS N.V., Eindhoven (NL)

(72) Inventors: Shriram Sethuraman, Lexington, MA (US); Balasundar Iyyavu Raju, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/968,887

(22) PCT Filed: Jan. 29, 2019

(86) PCT No.: PCT/EP2019/052038
§ 371 (c)(1),
(2) Date: Aug. 11, 2020

(87) PCT Pub. No.: WO2019/154667
PCT Pub. Date: Aug. 15, 2019

(65) Prior Publication Data
US 2021/0007707 A1 Jan. 14, 2021

Related U.S. Application Data

(60) Provisional application No. 62/629,194, filed on Feb. 12, 2018.

(51) Int. Cl.
*A61B 8/08* (2006.01)
*A61B 8/06* (2006.01)
*A61B 8/00* (2006.01)

(52) U.S. Cl.
CPC ............... *A61B 8/085* (2013.01); *A61B 8/06* (2013.01); *A61B 8/0891* (2013.01);
(Continued)

(58) Field of Classification Search
CPC ......... A61B 8/085; A61B 8/06; A61B 8/0891; A61B 8/4254; A61B 8/4444; A61B 8/461;
(Continued)

(56) References Cited

U.S. PATENT DOCUMENTS

| 11,413,015 B2 * | 8/2022 | Southard | C08G 61/124 |
| 2004/0015079 A1 * | 1/2004 | Berger | A61B 18/02 |
| | | | 600/437 |

(Continued)

OTHER PUBLICATIONS

Stebbings et al., "Resting Arterial Diameter and Blood Flow Changes With Resistance Training and Detraining in Healthy Young Individuals", Journal of Athletic Training 2013;48(2):209-219 (Year: 2013).*

(Continued)

*Primary Examiner* — Luther Behringer
*Assistant Examiner* — Amy Shafqat

(57) ABSTRACT

Systems, devices, and methods are provided to provide workflow assistance to an operator during a medical imaging procedure, such as a Doppler ultrasound evaluation of a body vessel of a subject. A sensor such as a gyroscope (128) may be integrated in an external ultrasound probe (102). Workflow assistance may be provided to position the ultrasound probe (102) to make accurate flow measurements of fluid within the vessel, such as by coupling system color flow information with gyroscope angles. The workflow assistance may also assist a user in identifying a perpendicular orientation of the ultrasound to be used as a reference in making Doppler measurements. The system may also be used to create a vessel map.

18 Claims, 8 Drawing Sheets

(52) U.S. Cl.
CPC .......... *A61B 8/4254* (2013.01); *A61B 8/4444* (2013.01); *A61B 8/4494* (2013.01); *A61B 8/461* (2013.01); *A61B 8/469* (2013.01); *A61B 8/488* (2013.01); *A61B 8/0858* (2013.01); *A61B 2562/0219* (2013.01)

(58) Field of Classification Search
CPC ......... A61B 8/469; A61B 8/488; A61B 8/464; A61B 8/00; A61B 8/42; A61B 8/463; G01S 7/52023; G01S 7/52068; G01S 7/52073
See application file for complete search history.

(56) References Cited

U.S. PATENT DOCUMENTS

| | | | | |
|---|---|---|---|---|
| 2009/0306509 | A1* | 12/2009 | Pedersen | A61B 8/4254 600/446 |
| 2014/0024944 | A1* | 1/2014 | Shau | A61B 8/4245 600/453 |
| 2014/0128739 | A1* | 5/2014 | Sundaran | A61B 8/54 600/459 |
| 2014/0303499 | A1* | 10/2014 | Toma | A61B 8/488 600/454 |
| 2014/0303501 | A1* | 10/2014 | Jin | A61B 8/4477 600/459 |
| 2015/0057544 | A1* | 2/2015 | Takagi | A61B 8/463 600/441 |
| 2015/0302638 | A1 | 10/2015 | Jago et al. | |
| 2015/0327841 | A1 | 11/2015 | Banjanin et al. | |
| 2017/0049419 | A1* | 2/2017 | Park | A61B 5/055 |
| 2017/0086785 | A1 | 3/2017 | Bjaerum | |
| 2019/0239848 | A1* | 8/2019 | Bedi | A61B 5/742 |
| 2022/0104886 | A1* | 4/2022 | Blanchard | A61B 8/0841 |

OTHER PUBLICATIONS

PCT/EP2019/052038 ISR & WO, Apr. 23, 2019, 15 Page Document.

* cited by examiner

WORKFLOW ASSISTANCE FOR MEDICAL DOPPLER ULTRASOUND EVALUATION

CROSS-REFERENCE TO PRIOR APPLICATIONS

This application is the U.S. National Phase application under 35 U.S.C. § 371 of International Application No. PCT/EP2019/052038, filed on Jan. 29, 2019, which claims the benefit of U.S. Provisional Patent Application No. 62/629,194, filed on Feb. 12, 2018. These applications are hereby incorporated by reference herein.

TECHNICAL FIELD

The present disclosure relates generally to providing workflow assistance to an operator during a medical imaging procedure, and in particular, during a Doppler ultrasound evaluation of a body vessel of a subject. Typical imaging procedures include imaging the vessel structure in the transverse view, manually aligning an ultrasound probe with the vessel in the longitudinal view, angle correction, and displaying velocities and manual sampling of potentially high velocity areas. Workflow assistance is provided by the present disclosure to simplify these steps and by measuring, displaying, and using an angle of an ultrasound probe in conjunction with other imaging parameters during the medical imaging procedure.

BACKGROUND

Cardiovascular diseases (CVD) have been on a steep rise since the last decade. The death toll recorded in 2008 was 17.3 million (about 30% of global deaths) and is estimated to reach 23.3 million by 2030. Heart disease and stroke form the major contributors to total loss due to CVD with 7.3 million and 6.2 million deaths respectively. Developing and under-developed nations of the world bear a greater part (almost 80%) of the total CVD burden. The national census of India 2010-11, recorded a staggering 0.3 million deaths due to diseases of circulatory system which comprised 29.8% of the total deaths.

Stroke is the second largest killer world-wide after coronary heart disease. About 50% of ischemic strokes are caused by unstable carotid artery plaque. Plaques are the deposition of cholesterol or blood cells on the inner walls of the blood vessel (stenosis) that constricts the lumen space and stiffens the vessels. Constriction in the arteries causes irregular and increased blood velocity. Further, limited flow in the carotid arteries could lead to neurological disturbance.

Non-invasive imaging of the carotid artery determined by B-mode ultrasonography, measuring carotid intima media thickness (CIMT) and plaque are increasingly used as surrogate markers for assessing preclinical and clinical atherosclerosis in the general and high-risk populations. In addition to anatomical structural thickening, blood flow is an indicator of degree of stenosis. For example, a peak systolic velocity (PSV)>125 cm/s is one such standard criterion that indicates >50% stenosis.

An ultrasound device including one or more ultrasound transducers may be positioned adjacent to the body of a patient and oriented toward the vessel. The transducers may emit ultrasonic energy and receive ultrasound echoes reflected from the vessel. The ultrasound echoes may be used to measure the thickness of tissue layers in the vessel as well as determine the rate of blood flow within the vessel. Ultrasound procedures are usually performed by an experienced sonographer. However, a non-expert operator may be called on to carry out a Doppler ultrasound procedure in some scenarios due to cost and geographical considerations, as well as other types of procedures, such as screening procedures. Both expert and non-expert operators may make routine errors in ultrasound procedures. For example, an operator may not accurately place a Doppler ultrasound device which may lead to errors in calculating medical data.

For example, carotid ultrasound evaluations are sometimes handled by novice or inexperienced sonographers. The carotid evaluation can be complicated for novices and even for experts because the user must first identify the carotid and then move the ultrasound transducer to best view and measure carotid intima media thickness and plaque. More specific problems resulting in an inefficient examination include incorrect Doppler angle and problems in identifying locations of high PSV.

SUMMARY

Systems, devices, and methods for performing ultrasound imaging are provided. The ultrasound imaging system may include an ultrasound probe with an ultrasound transducer array and a processor. The processor may be configured to receive imaging data from the ultrasound transducer, determine an angular position of the ultrasound probe, and transmit imaging data to a processing system. Aspects of the present disclosure provide workflow assistance to both expert and non-expert ultrasound operators during a Doppler exam. For example, the workflow assistance may assist a user in making accurate measurements without changing the orientation of the probe from a transverse to a longitudinal orientation. This may simplify procedures for a non-expert. The present disclosure may also include utilizing a sensor such as gyroscope integrated in the external ultrasound probe. With a simplified workflow that involves the coupling of color flow information with the gyroscope angles, the ultrasound probe can be positioned to make accurate PSV measurements. The perpendicular orientation when the flow transition (positive velocity to negative velocity or vice-versa) occurs can be accurately identified. Using this as a reference, the ultrasound probe can be positioned in an angle suitable for making Doppler measurements (e.g., Doppler angles<60 degrees). The system may also be used to create a vessel map.

Embodiments of the present disclosure provide an ultrasound imaging system that may include: an imaging probe configured to be positioned on a body of a subject, the imaging probe comprising: an ultrasound transducer array configured to obtain imaging data associated with blood flowing through a blood vessel within the body of the subject; a processor in communication with the ultrasound transducer array, the processor configured to: receive the imaging data from the ultrasound transducer array while the imaging probe is disposed at a plurality of angular positions with respect to the blood vessel of the subject; determine when the imaging probe is positioned perpendicularly with respect to the blood vessel based on the received imaging data; and thereafter output, to a first display device in communication with the processor, a visual representation of an angular position of the imaging probe with respect to the blood vessel.

In some embodiments, the visual representation of the angular position comprises a numerical value of the angular position. The imaging probe may include a housing, and the first display device may be coupled to the housing. The first display device may include at least one of a screen or an indicator light. The visual representation of the angular position may indicate when the imaging probe is disposed at a selected angular position with respect to the blood vessel. The selected angular position may be greater than or equal to 30 degrees from perpendicular.

In some embodiments, a processing system may be spaced from and in communication with the imaging probe, the processing system configured to: receive the imaging data from the processor of the imaging probe; and generate a graphical representation of the imaging data. The system may include a second display device in communication with the processing system and configured to output the graphical representation of the imaging data. The imaging data may be Doppler ultrasound data. The imaging probe may include a gyroscope.

In some embodiments, the processor is configured to determine the angular position of the imaging probe based on positional data from the gyroscope. The processor may be configured to receive the imaging data along a length of the blood vessel as the imaging probe is moved adjacent to the body, wherein the processor is configured to generate a vessel map representative of the length of the vessel based the imaging data. The processor may be configured to determine a location of the imaging probe with respect to the vessel map.

A method of ultrasound imaging is also provided, which may include: receiving, with an ultrasound transducer array coupled to an imaging probe positioned on a body of a subject, imaging data associated with blood flow through a blood vessel of the subject while the imaging probe is disposed at a plurality of angular positions with respect to the blood vessel of the subject; determining, with a processor within the imaging probe, when the imaging probe is positioned perpendicularly with respect to the blood vessel based on the received imaging data; transmitting, with the imaging probe to a first display device, the imaging data; and displaying, on the first display device, a visual representation of an angular position of the imaging probe with respect to the blood vessel.

In some embodiments, the imaging data is Doppler ultrasound data. The method may include displaying, on a second display device on the imaging probe, an indication of the angular position of the imaging probe. The method may include indicating, with the second display device, when the imaging probe is positioned at a 30 degree angle from perpendicular with respect to the vessel. The method may further include receiving imaging data along a length of the blood vessel as the imaging probe is moved adjacent to the body; and generating a vessel map representative of the length of the vessel based the imaging data. The method may include determining a location of the imaging probe with respect to the vessel map. In some embodiments, the vessel map comprises locations of vessel walls.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
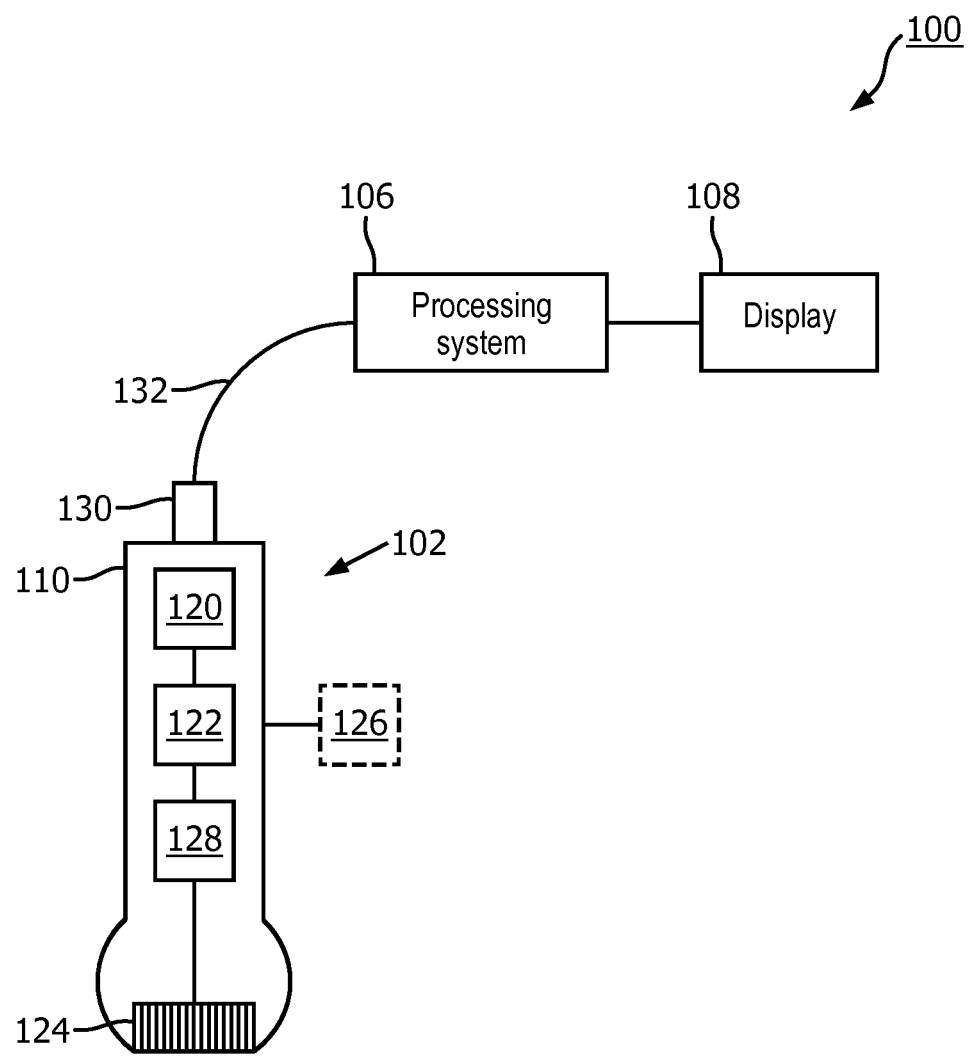
FIG. 1 is a diagrammatic schematic view of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 may include an imaging device 102, a processing system 106, and a display 108. The ultrasound imaging system 100 may be any type of imaging system suitable for use in visualizing the lumens or vasculature of a subject or patient. In some embodiments, the ultrasound imaging system 100 is a Doppler ultrasound imaging system. In some circumstances, the system 100 may include additional elements and/or may be implemented without one or more of the elements illustrated in FIG. 1.

In some embodiments, the imaging device 102 is sized and shaped to be placed on or near the anatomy of the subject to perform an ultrasound imaging procedure. The imaging device 102 may be placed directly on the body of the subject and/or adjacent the body of the subject. For example, the imaging device 102 may be directly in contact with the body of the subject while obtaining imaging data. In some embodiments, the device 102 includes one or more imaging elements which may be placed directly on or adjacent the body of the subject. In other embodiments, a housing of the imaging device is placed directly in contact with the body of the subject such that the imaging elements are adjacent the body of the subject. The subject may be a human patient or animal. The imaging device 102 may be portable and may be suitable to be used by a user in a medical setting. For example, the imaging device 102 may be a Doppler ultrasound imaging probe.

The imaging device 102 may include a housing 110, a memory 120, a processor 122, a transducer array, 124, a display 126, and a gyroscope 128. The housing 110 may surround and protect the various components of the imaging device 102. In some embodiments, the housing 110 is portable and may be sized and shaped for handheld grasping by an operator. The housing 110 may be suitable for sterilization processes. The housing 110 may include internal structure for securing the various components. For example, the transducer array may be placed in a compartment on a distal portion of the housing 110. The memory 120 and processor 122 may be disposed within a separate compartment of the housing 110.

The processor 122 of the device 102 may be configured to transmit signals to other elements device 102 as well as to external devices, such as the processing system 106 and display 108. The processor 122 may be an application-specific integrated circuit (ASIC), a field-programmable gate array (FPGA), a central processing unit (CPU), a digital signal processor (DSP), another hardware device, a firmware device, or any combination thereof configured to perform the operations described herein with reference to the processor 122 as shown in FIG. 1.

The processor 122 may be connected to a memory 120. In some embodiments, the memory 120 is a random access memory (RAM). In other embodiments, the memory 120 is a cache memory (e.g., a cache memory of the processor 122), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory 120 may include a non-transitory computer-readable medium. The memory 120 may store instructions. The instructions may include instructions that, when executed by a processor, cause the processor to perform operations described herein with reference to the processor 122 in connection with embodiments of the present disclosure.

The transducer array 124 may include a number of transducer elements. These elements may be placed in a one-dimensional or two-dimensional array. In some embodiments, the transducer elements of the array 124 are configured to emit ultrasound signals and receive ultrasound echo signals corresponding to the emitted ultrasound signals. The ultrasound echo signals may be processed by the processor 122, stored in the memory 120, and transmitted to the processing system 106 for further processing.

The device 102 may include a gyroscope 128. In some embodiments, the gyroscope 128 may be used to determine the orientation of the device 102 with respect to the body of the patient. For example, the gyroscope 128 may be used to determine the angle at which the device 102 is placed against the body of the patient. The processor 122 may receive data from the gyroscope that may ultimately be used to determine the angle at which the device 102 is placed relative to a vessel or lumen. The gyroscope 128 may be a microchip-packaged gyroscope, such as a microelectromechanical system (MEMS) gyroscope. In some embodiments, the gyroscope 128 includes an accelerometer. The gyroscope 128 may be configured for three, four, five, six, or other numbers of degrees of freedom.

The device 102 may be configured to assist an operator in achieving a correct Doppler angle for imaging purposes. An incorrect placement (location and orientation) of the sample volume (SV) measured by a medical imaging device may lead to erroneous PSV measurements. A Doppler angle of <60 degrees may improve imaging as this position may provide data closer to the true blood velocity in the vessel. In clinical practice, a sonographer may set the Doppler angle correction parameter of the imaging device to 60 degrees and manually orients the probe such that an angle correction cursor is parallel to the vessel wall. Such a work-step involves skill and is sometimes a routine step for an expert. For a non-expert operator such a step is challenging. To assist the non-expert, imaging as well as Doppler velocity measurements may be performed in the same orientation of the transducer (transverse) which can be done if the system provides assistance in indicating the appropriate Doppler angle. Therefore, the imaging device 102 of the present disclosure may include an indicator to tell the operator when the device 102 is oriented at a correct Doppler angle. This indicator may be a display 126 included with the device 102.

In some embodiments, the display 126 includes an indicator such as a screen or light that may be used to indicate an angular orientation of the device 102. For example, the display 126 may include screen that may be configured to display an angular measurement in numerical format. The angular measurement may correspond to a measurement of the gyroscope 128. In other embodiments, the display 126 includes an indicator light that may be configured to indicate when the device 102 is held at a certain angle relative to the body and/or vessel of a patient. For example, the indicator light may display a green color when the device 102 is held at perpendicular to the vessel and/or at a 30 degree angle with respect the vessel. In some embodiments, a 30 degree angle with respect to the vessel corresponds to a 60 degree angle with respect to the direction of flow within the vessel. The indicator light may be configured to display different colors depending on the angular orientation of the device 102. For example, the light may display a yellow color when the device 102 is held perpendicular to the vessel, red when the device 102 is held between 0 degrees to 30 degrees from normal with respect the vessel, and green when the device 102 is held between 30 and 60 degrees from normal with respect to the vessel. In other embodiments, the light may be green when the device is held over 60 degrees from normal with respect to the vessel. The display 126 may include other indicator methods (such as sound, vibration, blinking patterns, etc.) and other colors and measurements may also be used.

The device 102 may be connected to the processing system 106 via connection cable 132. The connection cable 132 may be connected to the device 102 via a connector 130 on a proximal portion of the device 102. The connection cable 132 may be any type of wired connection, such as a USB or Ethernet cable. In other embodiments, the device 102 is connected to the processing system 106 and/or display 108 via a wireless connection. In this case, the device 102 may include one or more wireless transmission devices, such as antennae. The one or more antennae may be disposed at a proximal portion of the device 102.

In some embodiments, the processing system 106 includes a processor that is separate from the processor 122 of the device 102. Image processing is completed by the processor 122 within the device 102 alone, by the processor in the processing system 106, or by any combination of these processors. Furthermore, the processors may be configured to produce a vessel map of the anatomy of the patient. For example, a sonographer may perform a transverse 2D sweep along the carotid tree and either takes Doppler color screen-shots of image slices that he or she suspects having high PSV values. In this transverse configuration, color flow data is obtained for the entire vessel cross-section. Without any assistance, an expert sonographer may get back to those locations in the longitudinal orientation to perform a detailed spectral Doppler measurement. For a non-expert, it may be challenging to get back to those high PSV locations without any assistance. Even if one succeeds in getting back to the location, switching orientation to make measurements is challenging. Therefore, the system 100 may be configured to prompt an operator to perform a sweep of the vessel with the device 102. As the device 102 receives and processes ultrasound imaging data, the processor 122 may be used to assign a vessel ID (including position, orientation, and landmark information) to certain images. This may allow an operator to return to areas of interest to perform further analysis or treatment.

It is understood that the system 100 and/or device 102 can be configured to obtain any suitable ultrasound imaging data. In some embodiments, the device 102 can include an imaging component of any suitable imaging modality, such as optical imaging, optical coherence tomography (OCT), etc. In some embodiments, the device 102 can include any suitable imaging component, including a pressure sensor, a flow sensor, a temperature sensor, an optical fiber, a reflector, a mirror, a prism, an ablation element, a radio frequency (RF) electrode, a conductor, and/or combinations thereof. Generally, the device 102 can include a transducer array 124 to obtain ultrasound data associated with the vessel or lumen. The device 102 may be sized and shaped (and/or configured) for insertion into a vessel or lumen of the patient.

The system 100 may be deployed in a medical laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as Doppler ultrasound imaging, angiography, fluoroscopy, computed tomography (CT), magnetic resonance imaging (MRI), intravascular ultrasound (IVUS), virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), intracardiac echocardiography (ICE), forward-looking ICE (FLICE), intravascular palpography, transesophageal ultrasound (TEE), and other medical imaging modalities, or combinations thereof. In some embodiments, device 102 may be controlled from a remote location such as the control room, such than an operator is not required to be in close proximity to the patient.

The imaging device 102 and display 108 may be communicatively coupled directly or indirectly to the processing system 106. These elements may be communicatively coupled to the processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

The imaging system 100 may be used to provide non-invasive imaging of body vessels or lumens, such as the carotid artery. This imaging may include B-mode ultrasonography and color flow maps. The system 100 may be used to measure carotid intima media thickness (CIMT) and plaque levels within vessels of a patient, which may be used as surrogate markers for assessing medical conditions such as atherosclerosis in patients. The system 100 may also be used to measure blood flow within the vessels of the patient, which may be an indicator of stenosis. In particular, Doppler parameters measured by the system 100 may be used to quantify carotid artery stenosis. These Doppler parameters may be any of peak systolic velocity (PSV), end diastolic velocity (EDV), internal carotid artery (ICA), external carotid artery (ECA) ratios, any combination of which may be used for quantification of carotid artery stenosis in the imaging system 100. For example, a Doppler parameter of PSV>125 cm/s may indicate>50% stenosis.

A comprehensive evaluation of the carotid arteries is typically performed by an experienced sonographer. However, there are scenarios in which carotid evaluation may be performed by a non-expert user. These scenarios include screening programs, cost and geographical considerations that may lead to difficulty in availability of quality healthcare, emergency care, and/or routine evaluations that may be performed at a primary care physician's office. Even outside these scenarios, even expert users may make routine errors in probe placement and orientation that may compromise accuracy of imaging procedures. Expert and non-expert operators of medical imaging systems would benefit from the methods and system 100 of this disclosure. For example, the system 100 may address inaccurate Doppler velocities due to incorrect Doppler angles by improved workflow systems, using a gyroscope (and/or other positional sensors) and indicating when devices are held at correct Doppler angles.

Figure 3:
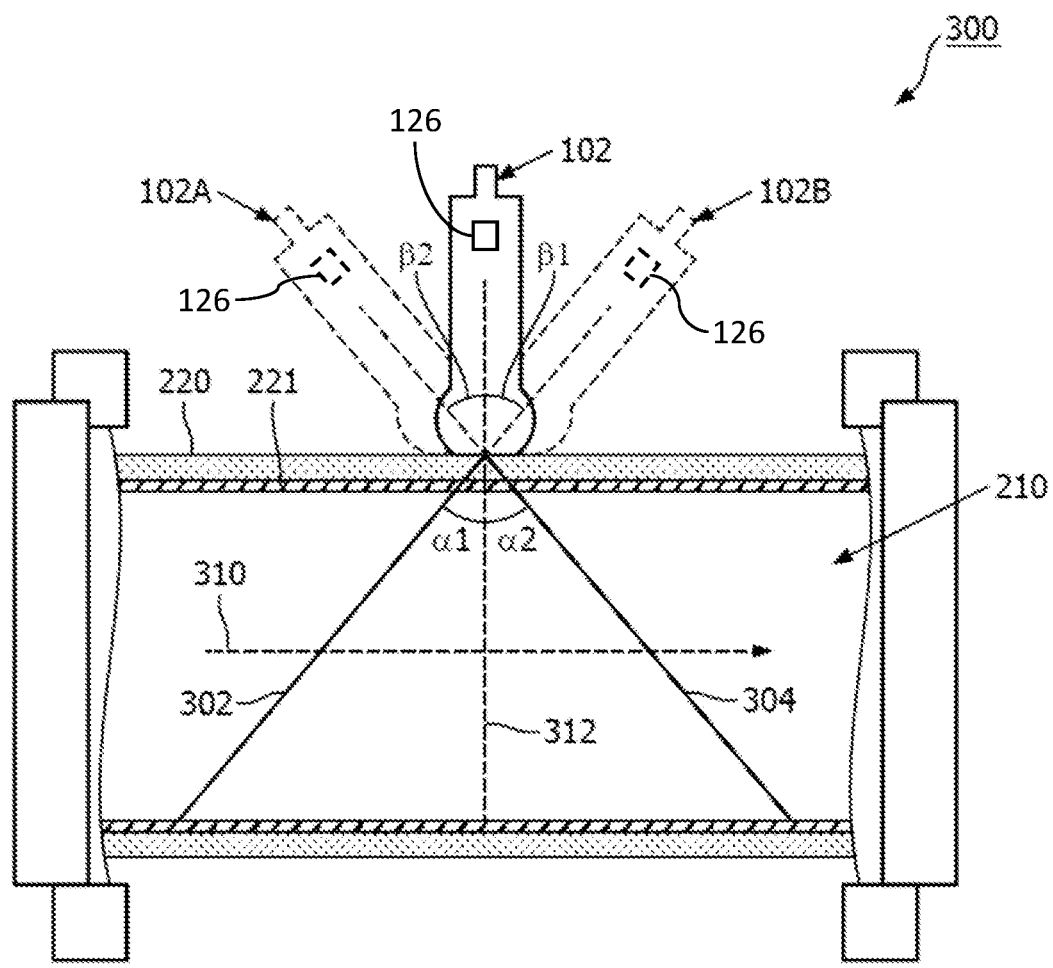
FIG. 3 is an exemplary illustration of an ultrasound imaging device in relation to a vessel, according to aspects of the present disclosure.
Figure 5:
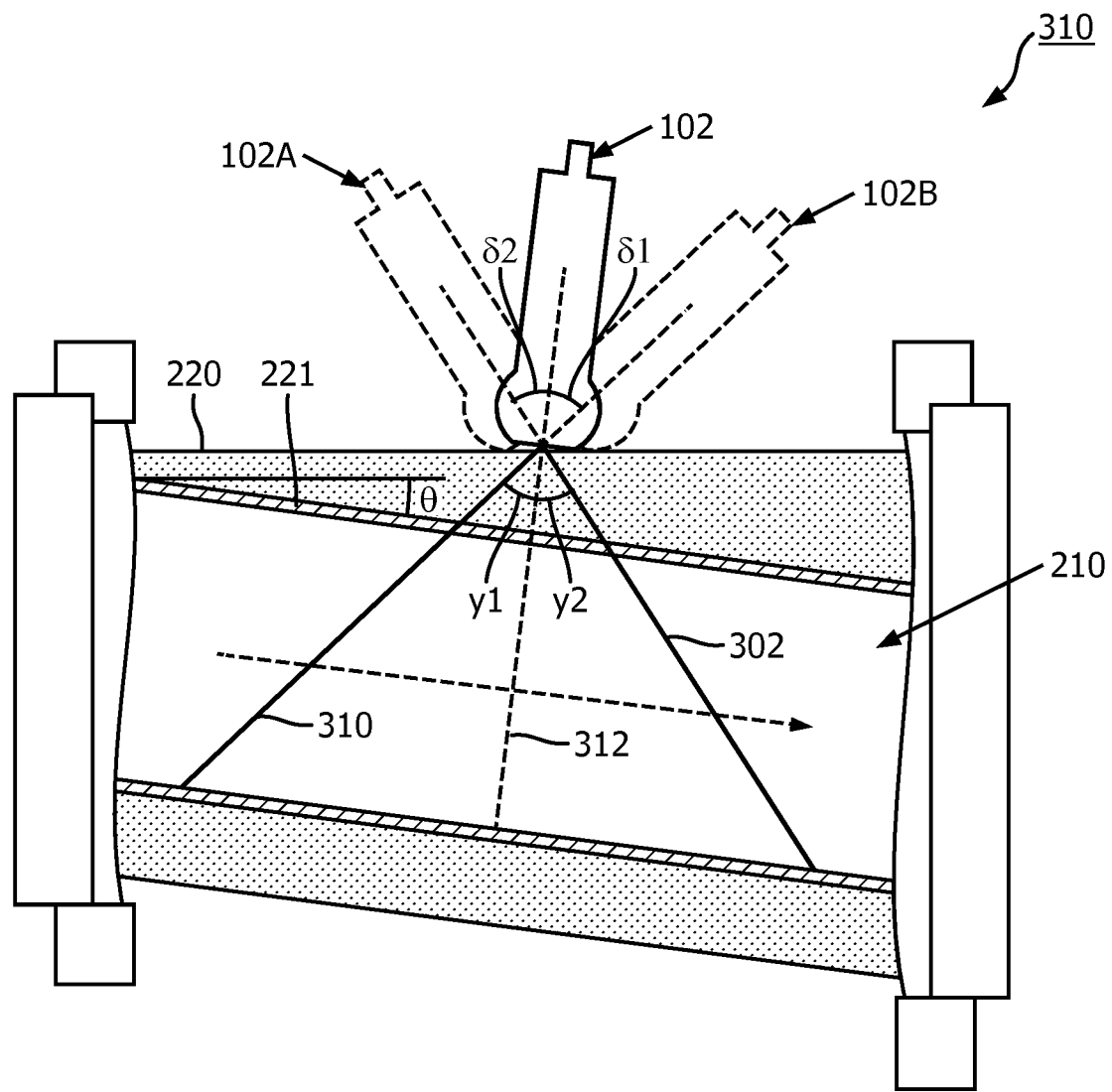
FIG. 5 is an exemplary illustration of an ultrasound imaging device in relation to a vessel, according to aspects of the present disclosure.

Generally, as further shown in FIGS. 3 and 5, the imaging device 102 may be configured to emit ultrasonic energy in order to create an image of a vessel or lumen and/or surrounding anatomy within the body of a patient. Ultrasonic waves emitted by a transducer array 124 of the device 102 may be reflected by discontinuities arising from tissue structures (such as the various layers of the vessel wall), red blood cells, and other features of interest. Echoes from the reflected waves are received by the imaging device 102 and passed along to the processing system 106. The processing system 106 processes the received ultrasound echoes to produce an image of the vessel or lumen and/or other portions of the anatomy of the patient based on the acoustic impedance associated with the ultrasound echoes. The image may be a two-dimensional cross-sectional image or a three-dimensional image of the vessel. The imaging device 102 and/or the processing system 106 may include features similar or identical to those found in commercially available ultrasound imaging elements such as the L12-4U Lumify probe and system, EPIQ, Affiniti, and/or CX50 ultrasound systems, each available from Koninklijke Philips N.V.

The imaging device 102 may be positioned outside the body of a patient. In some embodiments, the device 102 is positioned proximate to and/or in contact with the body of the patient near a vessel or lumen. The operator of the imaging device 102 may contact a distal portion of the imaging device to the body of the patient such that the anatomy is compressed in a resilient manner. The view of the anatomy shown in the ultrasound image depends on the position and orientation of the imaging device 102. To obtain imaging data of the vessel or lumen, the imaging device 102 can be suitably positioned either manually by a clinician and/or automatically by the operator so that the transducer array 124 emits ultrasound waves and receives ultrasound echoes from the appropriate portion of the vessel or lumen.

Imaging data obtained by the imaging device 102 can include velocity data and/or lumen data within a sample volume (SV) of the vessel. In the regard, the vessel includes anatomical structure, such as vessel walls that define the vessel or lumen, as well as fluid within the vessel or lumen. Fluid within the vessel or lumen may be moving relative to the imaging device 102. Lumen data obtained by the imaging device 102 may be representative of relatively stationary anatomy, including the vessel walls. The processing system 106 may be configured to generate a B-mode (brightness mode) imaging of anatomy corresponding to the varying acoustic impedance of the received ultrasound echoes. The lumen data can be used to evaluate the diameter, cross-sectional area, volume, and/or other geometric data associated with the vessel or lumen. The velocity data obtained by the imaging device 102 may be representative of the magnitude and/or the direction of fluid flow within the vessel or lumen. In that regard, the velocity data may be indicative of localized magnitude/direction of fluid flow (e.g., for each pixel in the image of the vessel or lumen). Various techniques exist for determining velocity data, including Doppler flow and vector flow. In Doppler flow imaging, the frequency shift associated with ultrasound energy obtained by the transducer array 124 is calculated and used to determine the speed and direction of the fluid flow. Doppler flow imaging may depend on angle of the transducer array 124 relative to the fluid flow and be limited to one-dimensional flow information. Vector flow imaging derives three-dimensional flow information from the ultrasound data obtained by the transducer array 124 so that angle-independent visualization of fluid flow is provided.

Figure 4:
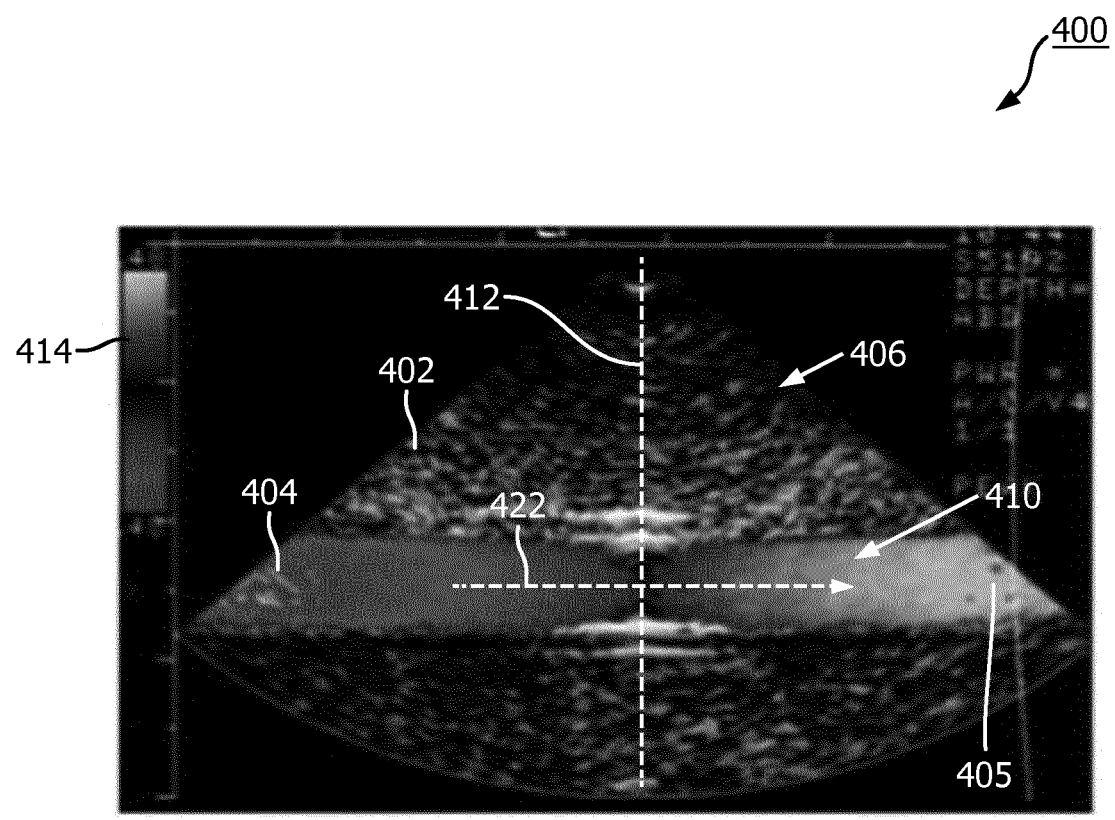
FIG. 4 is an exemplary illustration of an ultrasound image of a vessel, according to aspects of the present disclosure.

The lumen data and the velocity data may be combined for display on the display 108. In the example of FIG. 4, Doppler flow data may be illustrated as different colors indicative of varying magnitudes and direction of fluid flow, as provided in the key or legend 414. Vector flow data may be illustrated symbolically such as with arrows 310 (as shown in FIGS. 3 and 5) or 422 (as shown in FIG. 4) as having varying magnitudes and directions. The Doppler flow and/or vector flow data may be referenced as a velocity map that is overlaid on the B-mode image of the vessel or lumen illustrating the geometry of the vessel or lumen.

Generally, the device 102 can be utilized to visualize any suitable anatomy and/or body lumen of the patient. The processing system 106 outputs image data such that an image of the vessel or lumen, such as a cross-sectional image of the vessel or lumen, is displayed on the display 108. A vessel or lumen may represent fluid filled or surrounded structures, both natural and man-made. In some embodiments, the vessel or lumen is a blood vessel, such as the carotid artery. In addition to natural structures, the device 102 may be used to examine man-made structures such as, but without limitation, heart valves, stents, shunts, filters and other devices.

Figure 2A:
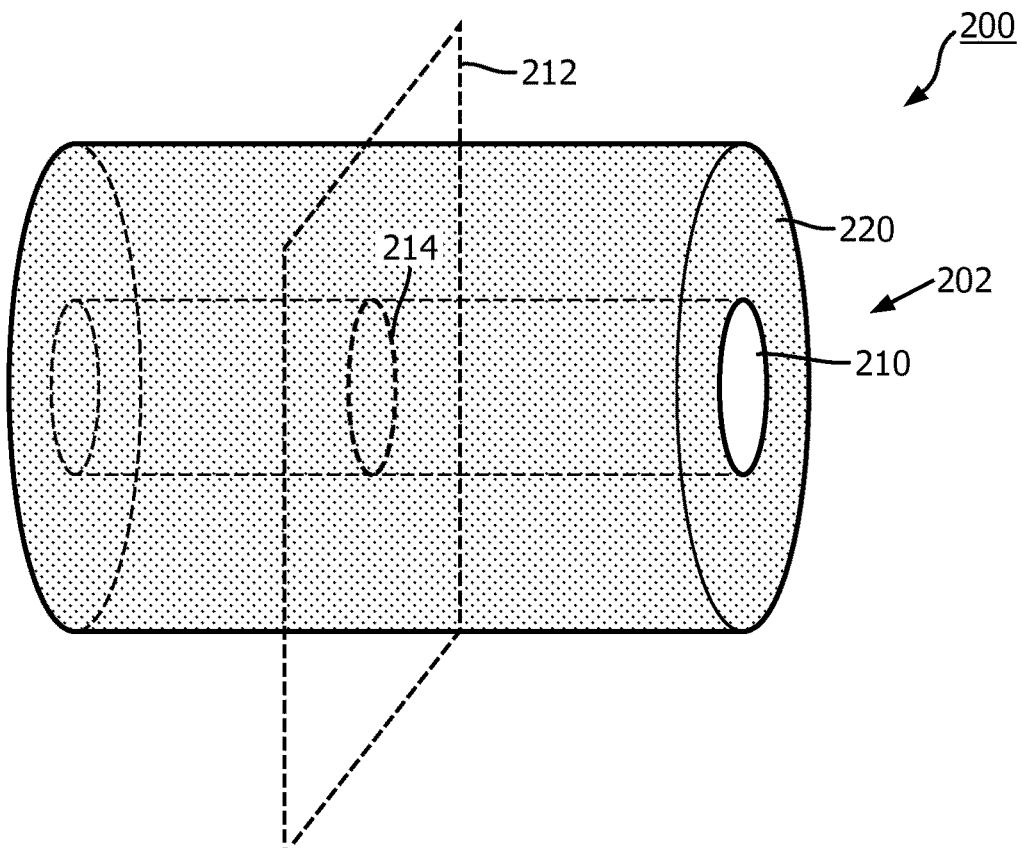
FIG. 2A is an exemplary cross-sectional view of a vessel, according to aspects of the present disclosure.

FIG. 2A shows a cross-sectional view 200 of a portion of anatomy 202 of a patient. The portion of anatomy 202 may include a vessel 210 and surrounding tissue 220. The vessel 210 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In some embodiments, the vessel 210 is a carotid artery. The ultrasound imaging system 100 may be configured to image a portion of the vessel 210. For example, the device 102 may be used to collect imaging data corresponding to a transverse plane 212 of the vessel 210. Collecting data on the transverse plane 212 may allow the system 100 to image outer borders 214 of the vessel 210, which may include the carotid intima media and other tissue layers. In some embodiments, the system 100 may use an image of a transverse plane 212 to determine when the device 102 is positioned perpendicular to the vessel. This perpendicular position may then be used to determine appropriate angles at which to position the imaging device 102 to correct accurate imaging data.

Figure 2B:
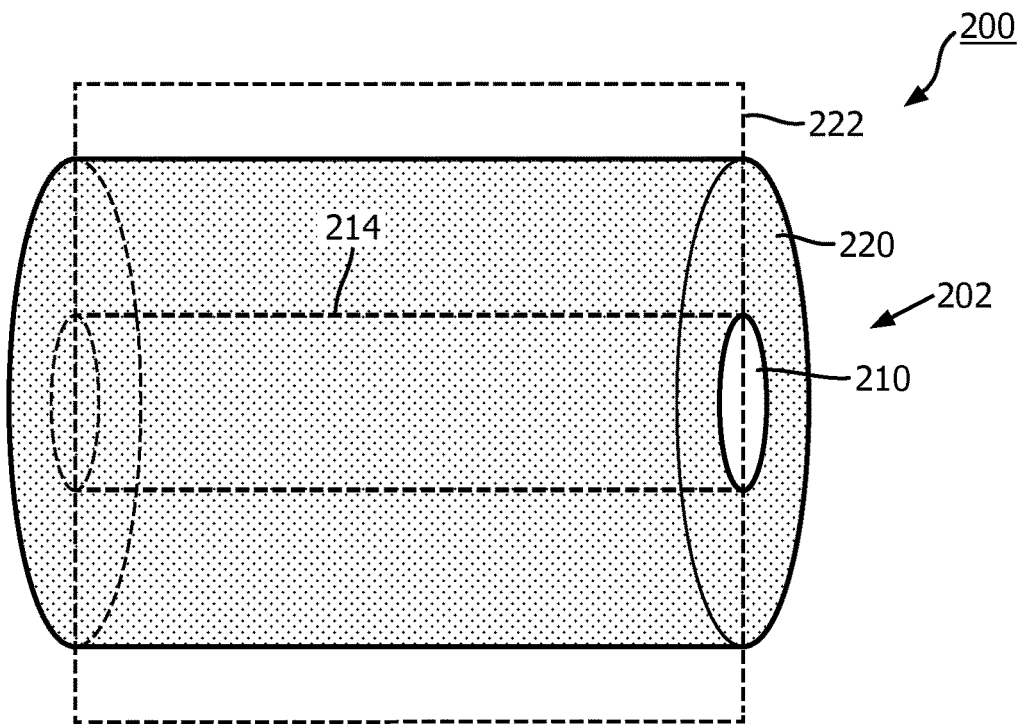
FIG. 2B is another exemplary cross-sectional view of a vessel, according to aspects of the present disclosure.

FIG. 2B shows a cross-sectional view 200 of a portion of anatomy 202 of a patient. In some embodiments, the system 100 may be may be used to receive imaging data corresponding to a longitudinal plane 222 of the vessel 210. Receiving data on the transverse plane 212 may allow the system 100 to image outer borders 224 along the length of the vessel 210. In some embodiments, imaging data is collected along the longitudinal plane to map the vessel. For example, the device 102 may be passed along a section of a vessel to determine its outer boundaries and physical features. Positional data and other measurements may be taken during this mapping procedure to assist an operator in identifying and revisiting areas of interest. For example, different areas of the vessel may be assigned a unique vessel ID during a mapping procedure. Imaging data may be correlated with the vessel ID to assist an operator in conceptualizing imaging data.

FIG. 3 is an exemplary illustration 300 of the imaging device 102 in relation to a vessel 210. The imaging device 102 may be placed adjacent the body of the patient. In some embodiments, the imaging device 102 is placed directly against tissue 220 of a patient, such as on an external extremity. For example, the imaging device 102 may be placed against the neck of a patient to image the carotid artery. The imaging device 102 may be translated across the surface of the tissue 220, for example, along the length of the vessel 210. The imaging device 102 may emit ultrasound signals into the tissue 220, vessel boundary 221, and vessel 210 of the patient. In some embodiments, the imaging device 102 may be oriented at different angles with respect to the tissue 220 and/or vessel 210. For example, the imaging device 102 may be positioned perpendicular to the vessel 210 along line 312. The imaging device 102 may then be "rocked" or tilted at to orientations 102A, 102B with various angles $\beta 1$ and $\beta 2$, as well as various angles in between, with respect to line 312. The ultrasound signals may be emitted at various angles α1 and α2, as well as various angles in between, with respect to line 312. The ultrasound signals may be emitted in a cone defined by outer boundaries 302, 304. In some embodiments, the imaging device 102 may be positioned an angle suitable for making Doppler measurements. For example, a Doppler angle of <60 degrees may provide accurate measurements of blood velocity in the vessel 210. The direction of the blood velocity may be shown by arrow 310 in FIG. 3. In some embodiments, the imaging device 102 may indicate the angle at which it is positioned relative to the vessel 210. In particular, a display 126 on the imaging device 102 may indicate when the device 102 is positioned perpendicular to the vessel 210 or when the angle 31 or 132 is positioned at 60 degrees from perpendicular, as well as other angular measurements.

FIG. 4 is an exemplary illustration of an ultrasound image 400 of a vessel 410 that may be produced by the system 100. In some embodiments, the imaging device 102 receives Doppler imaging data which may be processed by the processing system 106 to produce the image 400 of the vessel 410 and surrounding tissue 402. The image 400 shows an imaging cone 406 which shows a portion of a vessel 410 that is imaged by sweeping the imaging device 102 at various angles with respect to the vessel 410. The velocity of blood flowing within the vessel 410 may be visualized using colors shown on legend 414. In some embodiments, velocity measurements may be used by the system 100 to determine when the device 102 is positioned perpendicular to the vessel 410. For example, the Doppler data received by the device 102 shows a change in the direction of flow along line 412 by the change of color from red to blue. This change in color may indicate flow toward the probe on one side (404) and flow away from the probe on the other side (405). The location of change may indicate where the device 102 is positioned perpendicular to the vessel. This technique may be used even when the vessel is not parallel to the external surface of the body, as shown in FIG. 5. The perpendicular position of the device 102 may be used to determine acceptable Doppler angles at which to orient the device 102 to receive accurate images of the vessel.

FIG. 5 is an exemplary illustration of an imaging device 102 in relation to a vessel 210 that is not parallel to an outer surface of tissue 220. In the example of FIG. 5, the vessel 210 is oriented at an angle θ with respect to the outer surface of tissue 220. A device 102 may be placed against the tissue 220. The device 102 may be used to image the vessel 210 and surrounding tissue. In this case, the device 102 may be positioned perpendicular to the vessel 210 by finding the change in direction of velocity of blood within the vessel 210, as discussed above in reference to FIG. 4. Once the perpendicular orientation is determined (i.e., along line 312) the operator may rock the device 102 at angles 61 and 62 from perpendicular. In some embodiments, the angles 61 and 62 may be chosen by the operator based on Doppler parameters. For example, angle δ1 may measure 60 degrees and angle δ2 may measure −60 degrees with respect to the perpendicular line 312. As the device 102 is rocked, the ultrasound signals may be emitted by the device along angles from γ1 to γ2. This may allow the system to accurately image a vessel 210 regardless of its orientation in the body, which may assist an operator in obtaining more accurate Doppler images of the vessel.

Figure 6:
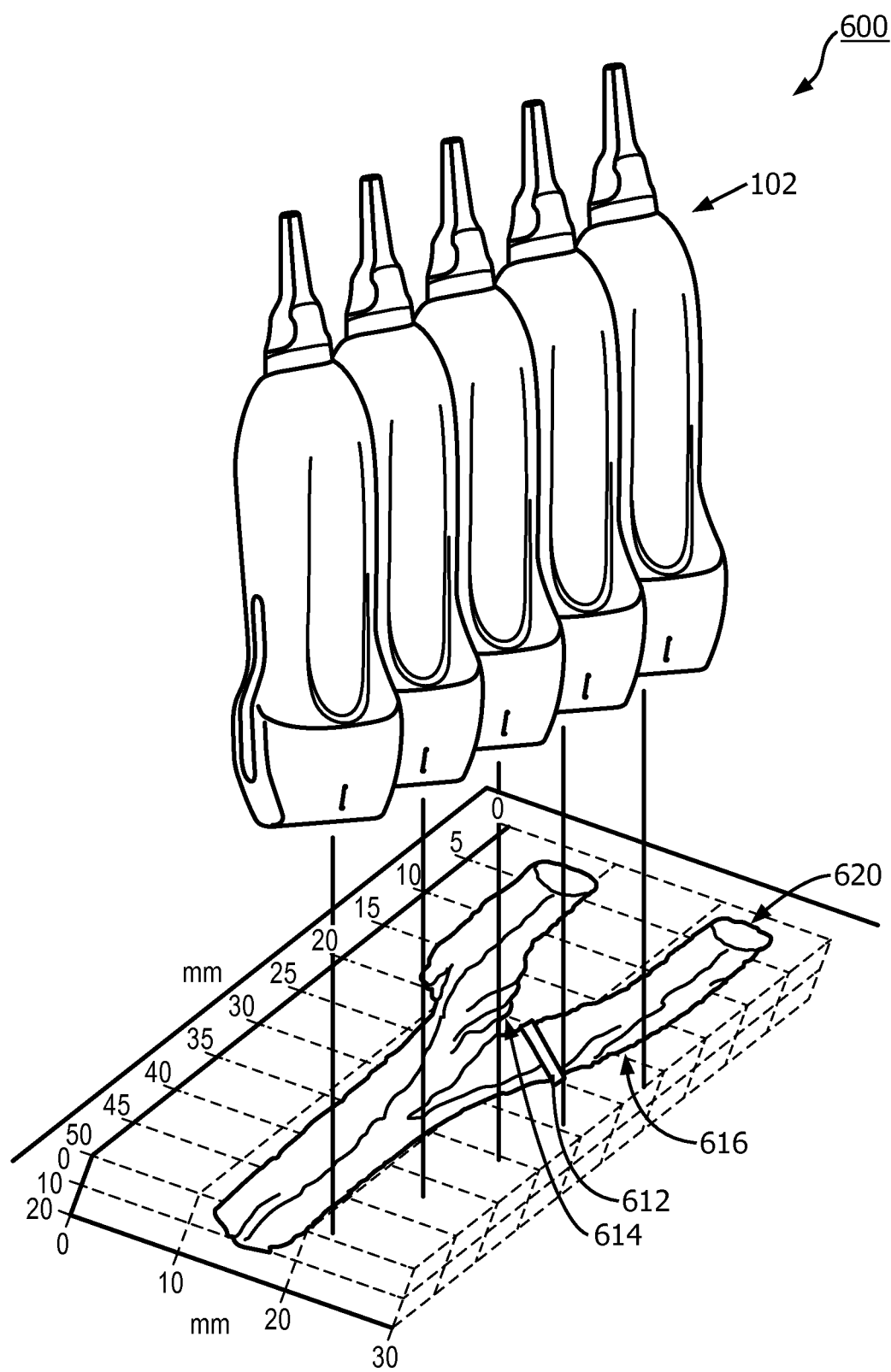
FIG. 6 is an exemplary illustration of an ultrasound imaging device and a vessel, according to aspects of the present disclosure.

FIG. 6 shows an exemplary view 600 of an imaging device 102 that is moved along a vessel 620. In some embodiments, an operator may use the ultrasound imaging system 100 to perform a sweep of the carotid artery to collect Doppler images of the vessel 620. These images may be used to determine areas of interest with a high peak systolic velocity (PSV), such as location 612. The images may be used to determine B-mode and color flow data for a portion of the vessel 620 cross-section. An experienced operator may be able to return to the area of interest to collect further data, but an inexperienced operator may not be able to find these locations a second time. Therefore, the ultrasound imaging system 100 may be used to gather positional information during imaging operations which may be correlated to the images. This may assist an operator in returning to areas of interest after an initial sweep of the vessel.

In one embodiment, the system 100 may assign a unique vessel ID to each set of imaging data collected by the device 102. The vessel ID may be a number, letter, symbol, or any combination of these. The vessel ID may be based on one or more landmarks within the vessel 620, such as a bifurcation or notch. The vessel ID may identify a particular branch or other subdivision of the vessel 620. For example, as the device 102 is moved across the vessel 620 and receives images for location 612, the system may assign a vessel ID to location 612. The vessel ID may be added to the ultrasound data collected at location 612, such that the vessel ID may be used to determine the location 612 at a later time. In some embodiments, the vessel ID for the location 612 includes a distance from bifurcation 614 (in mm) and identifies branch 616. The vessel ID may be displayed on a display 108 along with imaging data.

Figure 7:
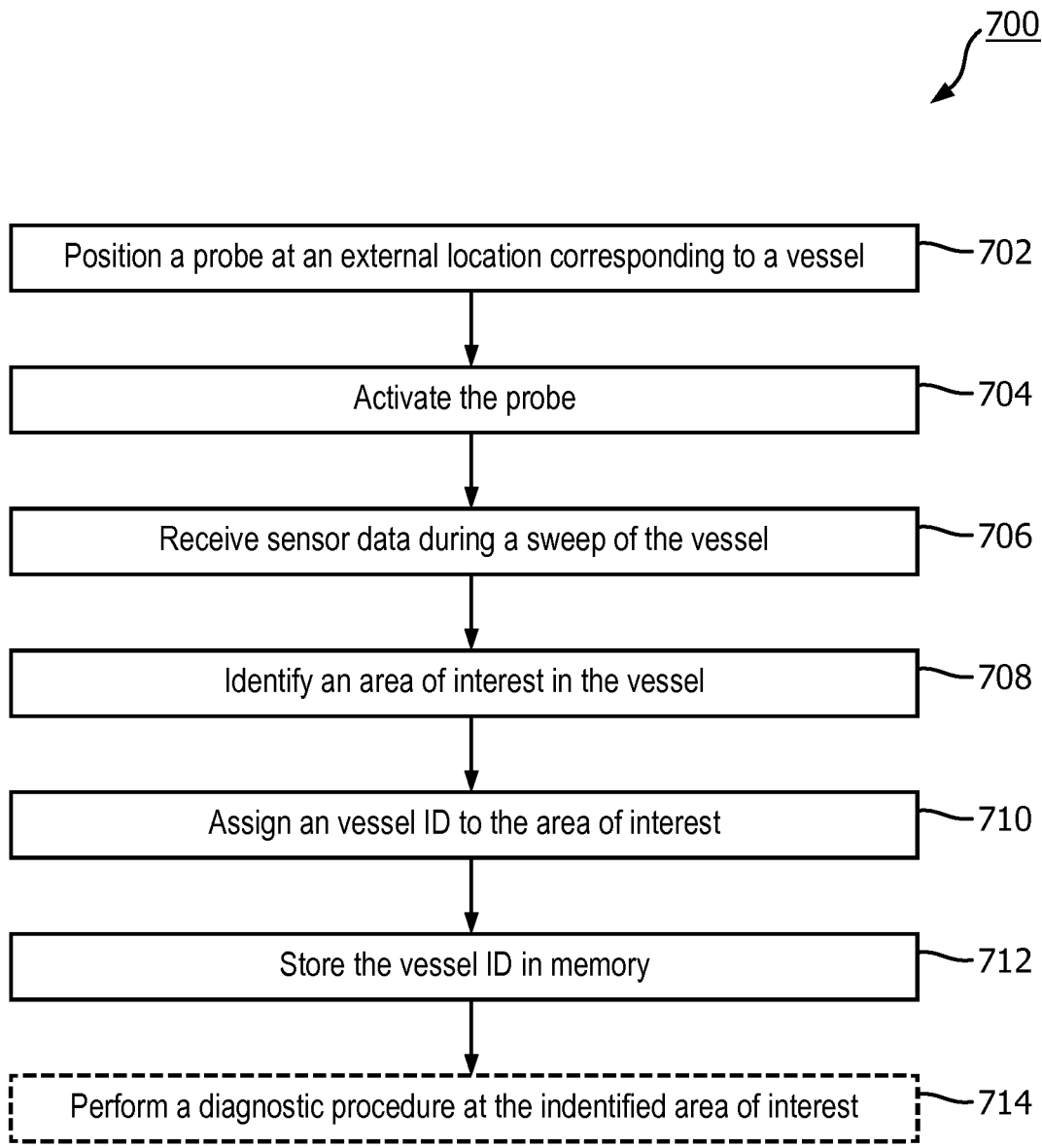
FIG. 7 is a flow diagram of a method of ultrasound imaging according to aspects of the present disclosure.

FIG. 7 is a flow diagram of a method 700 of ultrasound imaging. In some embodiments, the steps of the method 700 may be carried out by the ultrasound imaging system 100 and associated components as shown in FIG. 1. It is understood that the steps of method 700 may be performed in a different order than shown in FIG. 7, additional steps can be provided before, during, and after the steps, and/or some of the steps described can be replaced or eliminated in other embodiments.

At step 702, the method 700 may include positioning a probe at an external location corresponding to a vessel. In some embodiments, the probe is an ultrasound imaging device such as imaging device 102. The vessel may be any body lumen, including veins and arteries. In some embodiments, the vessel is the carotid artery. The probe may be positioned against the body of the patient, such as on the patient's neck. In some embodiments, the system 100 may receive and store an initial or "zero" position of the probe. The zero position may be used to map the vessel. The zero position may be recorded by inputting the position into the probe. For example, the probe may include a button, switch, or other input device that may be pressed when the probe is positioned at the zero position. In some embodiments, this input device is a button located on a handle of the probe. This may cause the probe to automatically store the zero position of the probe.

At step 704, the method 700 may include activating the probe. The probe may be used to emit ultrasound signals into the anatomy of the patient. The probe may receive ultrasound echo signals corresponding to the emitted signals which may be used to image areas of the vessel. In some embodiments, the probe is moved or swept along the vessel after activation.

At step 706, the method 700 may include receiving sensor data during a sweep of the vessel. The sensor data may be received by a transducer within in the probe, such as transducer array 124 as shown in FIG. 1. The sensor data may include Doppler imaging data such as B-mode and color flow data. The sensor data may include individual image slices and vessel boundary data. In some embodiments, the probe is used to perform a longitudinal sweep of the vessel.

At step 708, the method 700 may include identifying an area of interest. An area of interest may be located at any point along the vessel. The area of interest may be identified based on Doppler imaging data. For example, an area of interest may be identified with a high PSV value. Areas of interest may also be identified based on landmarks in the vessel. For example, an operator may wish to view a certain branch of a vessel system. The operator may wish to return the area of interest to conduct further diagnostic procedures at a later time.

At step 710, the method 700 may include assigning a vessel ID to the area of interest. In some embodiments, a vessel ID is assigned to every image collected by the system along the vessel. The vessel ID may be displayed with the received images so that an operator may identify the location of the image with respect to the vessel. In other embodiments, only certain areas of interest are assigned vessel IDs. For example, an operator may find a high PSV value in a portion of the vessel and may wish to tag the area for future diagnostic procedures. The vessel ID may include Doppler data including PSV measurements and color flow data, as well as coordinates along the vessel. The vessel ID may be correlated with the image data. The vessel IDs may be compiled into a vessel map of the vasculature of the patient. For example, the operator may collect imaging data along the length of the carotid artery. Each individual image is assigned a vessel ID, which together form an encoded vessel map of the carotid artery of patient. The operator may then return may then use the images and corresponding vessel IDs to return to a specific area of the carotid artery for further imaging or treatment. The vessel may be generated using a processor within the probe, with an external processing system, or a combination of these processors.

At step 712, the method 700 may include storing the vessel ID in memory. In some embodiments, the vessel ID is stored with the image data in a memory device, such as memory 120 as shown in FIG. 1. The vessel ID may be search independently to allow the operator to identify images associated with the vessel ID.

At step 714, the method 700 may optionally include performing a diagnostic procedure at the identified area of interest. In this case, the operator may use the vessel ID and/or correlated information to return to an area of interest in the vessel. For example, the operator may return to an area of interest to conduct another Doppler imaging procedure, another type of imaging procedure, or to treat the area of interest. The area of interest may also be revisited by an operator in an diagnostic procedure, such as an ultrasound imaging procedure.

Figure 8:
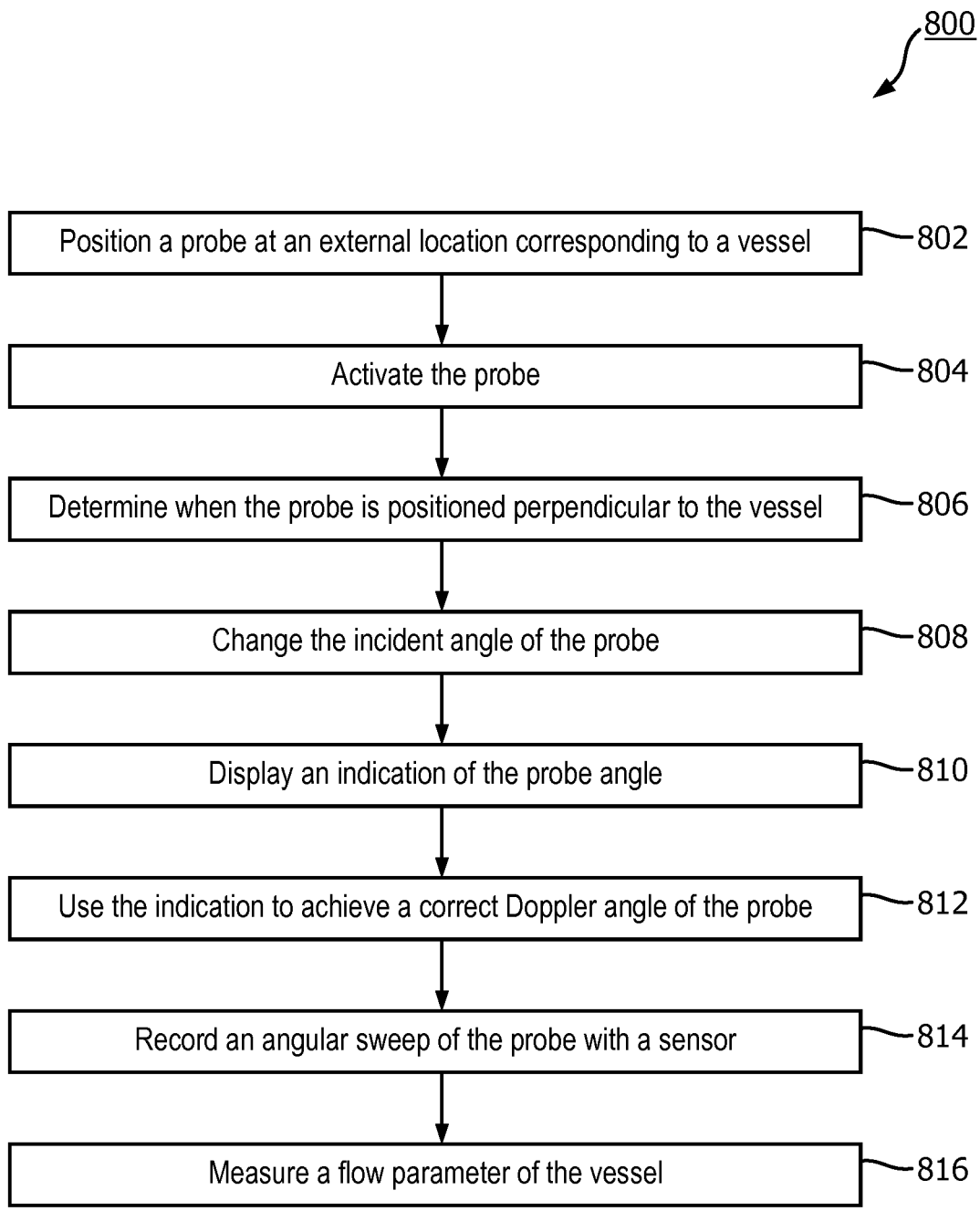
FIG. 8 is a flow diagram of another method of ultrasound imaging according to aspects of the present disclosure.

FIG. 8 is a flow diagram of a method 800 of ultrasound imaging. In some embodiments, the steps of the method 800 may be carried out by the ultrasound imaging system 100 and associated components as shown in FIG. 1. It is understood that the steps of method 800 may be performed in a different order than shown in FIG. 8, additional steps can be provided before, during, and after the steps, and/or some of the steps described can be replaced or eliminated in other embodiments.

At step 802, the method 800 may include positioning a probe at an external location corresponding to a vessel. In some embodiments, the probe is an ultrasound imaging device such as imaging device 102. The vessel may be any body lumen, including veins and arteries. In some embodiments, the vessel is the carotid artery. The probe may be positioned against the body of the patient, such as on the patient's neck.

At step 804, the method 800 may include activating the probe. The probe may be used to emit ultrasound signals into the anatomy of the patient. The probe may receive ultrasound echo signals corresponding to the emitted signals which may be used to image areas of the vessel. In some embodiments, the probe is moved or swept along the vessel after activation.

At step 806, the method 800 may include determining when the probe is positioned perpendicular to the vessel. In some embodiments, this determination is made by collecting Doppler imaging data of the velocity of blood flow in the vessel, for example, in a transverse view of the vessel. In particular, the probe may be used to determine a transition line between blood flowing toward the probe and blood flowing away from the probe. This line may represent where the probe is perpendicular to the vessel, such as line 412 as shown in FIG. 4. In some embodiments, an indicator on the probe may alert the operator that the probe is perpendicular to the vessel. For example, the Doppler imaging data may be collected and analyzed by the system 100 automatically, such that the system 100 determines a line perpendicular to the vessel. When the probe is placed on this line, an indicator such as a screen or indicator light on the probe may be activated to notify the operator that the probe is perpendicular to the vessel.

At step 808, the method 800 may include changing the incident angle of the probe. In some embodiments, the probe is rocked back and forth to image a cone-shaped area within the vessel. Orienting the probe at various angles may help to collect more accurate imaging results. For example, ultrasound emissions that travel with a Doppler angle of <60 degrees with respect to a vessel may provide imaging results that show accurate blood velocity in the vessel. In some embodiments, the probe is rocked back and forth 60 degrees with respect to the perpendicular orientation determined in step 806. In other embodiments, the probe is rocked at 45, 50, 75, 80, or 85 degrees in either direction, as well as other values.

At step 810, the method 800 may include displaying an indication of the probe angle. In some embodiments, the probe includes a display, such as a screen or indicator light. This display may be used to indicate the angle of the probe with respect to the vessel and/or anatomy of the patient. For example, the probe may include a gyroscope or other type of position sensor that may be used to determine the angular orientation of the probe. The position sensor data may be received a processing system which may determine an acceptable Doppler angle for the probe to gather accurate imaging data, such as PSV measurements. This angle may be displayed or otherwise indicated on the probe. For example, the probe may display the angle in numerical format or as an indicator light on the probe. In particular, an indicator light on the probe may flash green when the probe is oriented perpendicular to the vessel, at or greater than a 30 degree angle from perpendicular to the vessel, or <60 degree angle with respect to the direction of flow. Other types of indicators may be used, such as colored lights, graphical displays, vibration devices, or other indicators. In some embodiments, a display of the probe angle is shown on an external display, such as display 108 as shown in FIG. 8. The indication of the probe angle may assist an operator in quickly collecting accurate Doppler ultrasound images.

At step 812, the method may include using the indication of the probe angle to achieve a correct Doppler angle of the probe. As discussed above, a Doppler angle of 60 degrees may be chose to show accurate blood velocity measurements in the vessel. Other measurements may also be chosen, such as 65, 75, 80, 85, or 90 degrees.

At step 814, the method may include recording an angular sweep of the probe with a sensor. In some embodiments, the sensor is the transducer array 124 as shown in FIG. 1. The angular sweep of the sensor may be used to image a cone-shaped area within the vessel, as shown in FIGS. 3-5. This imaging data may be sent from the probe to an external processing system to be viewed by a user.

At step 816, the method 800 may include measuring a flow parameter of the vessel. In some embodiments, the imaging data collected by the probe during the angular sweep is processed to produce an image of the vessel showing flow parameters. The flow parameters may be shown as a B-mode image or color flow map as shown in FIG. 4. The flow parameters may be displayed in other graphical formats (for example, by shaded or colored lines or regions) as well as textually (for example, in text boxes). The flow parameters may also include recommendations for further diagnostic procedures or treatment. The steps of method 700 and 800 may be used to guide an operator during an ultrasound imaging procedure to produce accurate imaging results. In particular, the methods 700 and 800 may allow inexperienced and experienced operators alike to quickly determine areas of interest, track the locations of the areas of interest along a vessel, and perform accurate Doppler imaging procedures.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
an imaging probe configured for handheld operation by a user;
an ultrasound transducer array within the imaging probe and configured to obtain imaging data associated with blood flow through a blood vessel within a body of a subject, wherein the imaging data comprises Doppler data;
a first display device on the imaging probe and comprising an indicator light; and
a processor within the imaging probe and in communication with the ultrasound transducer array and the first display device, wherein the processor configured to:
during a first portion of an imaging procedure:
receive the imaging data from the ultrasound transducer array while the imaging probe is moved to be in a plurality of orientations;
identify, based on the imaging data, a transition between a positive velocity of the blood flow and a negative velocity of the blood flow; and
determine, based on the transition, a perpendicular orientation of the imaging probe in which the imaging probe is positioned at a perpendicular angle with respect to the blood vessel; and
during a second portion of the imaging procedure that occurs after the first portion:
determine, using the perpendicular orientation as a reference, an angle of the imaging probe with respect to the blood vessel while the imaging probe is in a first orientation; and
output, to the first display device, a visual representation of the angle for the user, wherein the visual representation of the angle comprises a color of the indicator light, wherein the color is representative of a numerical value of the angle such that the indicator light changes to a different color when the imaging probe is moved to be in a second orientation in which the imaging probe is positioned at a different angle with respect to the blood vessel.

2. The ultrasound imaging system of claim 1, wherein the screen is configured to display the numerical value of the angle.

3. The ultrasound imaging system of claim 1, wherein the first display device further comprises a screen.

4. The ultrasound imaging system of claim 1, wherein the visual representation of the angle indicates when the imaging probe is disposed at a selected angle with respect to the blood vessel.

5. The ultrasound imaging system of claim 4, wherein the selected angle is greater than or equal to 30 degrees from the perpendicular angle.

6. The ultrasound imaging system of claim 1, further comprising a processing system spaced from and in communication with the imaging probe, wherein the processing system is configured to:
receive the imaging data from the processor of the imaging probe; and
generate a graphical representation of the imaging data.

7. The ultrasound imaging system of claim 6, further comprising a second display device in communication with the processing system and configured to output the graphical representation of the imaging data.

8. The ultrasound imaging system of claim 1, wherein the imaging probe further comprises a gyroscope.

9. The ultrasound imaging system of claim 8, wherein the processor is configured to determine the angle of the imaging probe based on data from the gyroscope.

10. The ultrasound imaging system of claim 1,
wherein the processor is further configured to receive the imaging data along a length of the blood vessel as the imaging probe is moved adjacent to the body, and
wherein the processor is configured to generate a vessel map representative of the length of the vessel based on the imaging data.

11. The ultrasound imaging system of claim 10, wherein the processor is configured to determine a location of the imaging probe with respect to the vessel map.

12. The ultrasound imaging system of claim 1, wherein the color of the indicator light comprises:
a first color when the angle is a first angle with respect to the blood vessel;
a second color when the angle is between the first angle and a second angle with respect the blood vessel; and
a third color when the angle is between the second angle and a third angle with respect the blood vessel.

13. A method of ultrasound imaging, comprising:

during a first a first portion of an imaging procedure:

receiving, with a processor within an imaging probe under handheld operation by a user, imaging data obtained by an ultrasound transducer array within the imaging probe, wherein the imaging data is associated with blood flow through a blood vessel within a body of a subject, wherein the imaging data comprises Doppler data, wherein the imaging data is received while the imaging probe is moved to be in a plurality of orientations;

identifying, with the processor, a transition between a positive velocity of the blood flow and a negative velocity of the blood flow, based on the imaging data; and determining, with the processor, a perpendicular orientation of the imaging probe in which the imaging probe is positioned at a perpendicular angle with respect to the blood vessel; and during a second portion of the imaging procedure that occurs after the first portion:

determining, with the processor, an angle of the imaging probe with respect to the blood vessel while the imaging probe is in a first orientation, using the perpendicular orientation as a reference; and outputting, to a first display device on the imaging probe, a visual representation of the angle for the user, wherein the first display device comprises an indicator light, wherein the visual representation of the angle comprises a color of the indicator light, wherein the color is representative of a numerical value of the angle such that the indicator light changes to a different color when the imaging probe is moved to be in a second orientation in which the imaging probe is positioned at a different angle with respect to the blood vessel.

14. The method of claim 13, wherein the visual representation of the angle indicates when the imaging probe is positioned at a 30 degree angle relative to the perpendicular angle.

15. The method of claim 13, further comprising:

receiving the imaging data along a length of the blood vessel as the imaging probe is moved adjacent to the body; and generating a vessel map representative of the length of the vessel based on the imaging data.

16. The method of claim 15, further comprising determining a location of the imaging probe with respect to the vessel map.

17. The method of claim 15, wherein the vessel map comprises locations of vessel walls.

18. The method of claim 13, further comprising transmitting, with the imaging probe to a second display device, the imaging data.

* * * * *